(12) United States Patent
Kwok et al.

(10) Patent No.: US 12,410,432 B2
(45) Date of Patent: Sep. 9, 2025

(54) L-RNA APTAMER CYCLIZATION AND USE THEREOF

(71) Applicant: City University, Kowloon (HK)

(72) Inventors: Chun Kit Kwok, Kowloon (HK); Danyang Ji, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 974 days.

(21) Appl. No.: 17/236,600

(22) Filed: Apr. 21, 2021

(65) Prior Publication Data
US 2022/0348922 A1    Nov. 3, 2022

(51) Int. Cl.
*C12N 15/115*    (2010.01)
*C12Q 1/68*    (2018.01)

(52) U.S. Cl.
CPC ........ *C12N 15/115* (2013.01); *C12N 2310/16* (2013.01)

(58) Field of Classification Search
None
See application file for complete search history.

(56) References Cited

U.S. PATENT DOCUMENTS

2023/0104113 A1*  4/2023  Kahvejian .......... A61K 31/7105
514/44 A

OTHER PUBLICATIONS

Kumar et al. J. Am. Chem. Soc. vol. 129:6859-6864, 2007.*
Fantoni et al. Chem. Rev. vol. 121:7122-7154, Jan. 1, 2021.*
Umar et al. Nucleic Acids Research, vol. 48:10125-10141, 2020.*

* cited by examiner

*Primary Examiner* — Sean McGarry
(74) *Attorney, Agent, or Firm* — Conley Rose, P.C.; Michael W. Piper; Andrew M. Metrailer (57) ABSTRACT

A method of cyclizing an L-RNA aptamer by modifying the aptamer with a 3' azide and a 5' alkyne group and using click chemistry reaction-based method. The cyclized L-RNA aptamers have improved binding properties and favour more in vitro/cell applications. Also disclosed is an L-oligonucleotide aptamer having linked ends.

7 Claims, 8 Drawing Sheets

Specification includes a Sequence Listing.

L-RNA APTAMER CYCLIZATION AND USE THEREOF

SEQUENCE LISTING TXT

The present application is being filed along with a Sequence Listing TXT in electronic format. The Sequence Listing TXT is provided as an TXT file entitled HP0145US_SEQ_AF_ST25, created Jan. 7, 2025, which is 5 Kb in size. The information in the electronic format of the Sequence Listing TXT is incorporated herein by reference in its entirety.

TECHNICAL FIELD

The present disclosure generally relates to aptamers and more particularly methods for cyclization of L-RNA aptamers to provide molecules having resistance to nuclease degradation and improved target recognition performance.

BACKGROUND

Antibodies are the most widely used class of bioreceptors for sensing purposes. Antibodies are typically used both in the scientific community and commercially. Nevertheless, the shortcomings associated with antibodies have fueled interest in alternative reagents such as aptamers.

SUMMARY

Disclosed herein is a method of cyclizing an aptamer comprising: synthesizing an L-RNA aptamer with a 3' azide residue and a 5' terminal alkyne group; and ligating the L-RNA aptamer with a 3' azide residue and a 5' terminal alkyne group using intramolecular click chemistry reaction under the catalysis of Cu(I) to form a cyclized aptamer.

In a first aspect, the disclosure proposes a method of linking two terminal ends of oligonucleotide, wherein one of the terminal oligonucleotide ends has a 5' terminal alkyne; and the other one of the terminal oligonucleotide ends has a 3' azide residue; the method comprising the step of: linking the 5' terminal alkyne to the 3' azide residue.

Alternatively, the step of linking the 5' terminal alkyne to the 3' azide residue to place in the presence of a catalyst for azide-alkyne cycloaddition. Typically, the catalyst is Cu(I). Optionally, the Cu is provided in a higher oxidation state, together with a reducing agent to reduce the Cu in a higher oxidation state to Cu(I). For example, the Cu is provided in the form of copper (II) complex with the ligand tris(benzyltriazolylmethyl)amine, and the the reducing agent is ascorbic acid or its salt.

Optionally, the two terminal ends of oligonucleotide are from a single strand of RNA, such as L-Apt.4-1c. Alternatively, the two terminal ends of oligonucleotide are from two unconnected strands of RNA.

Typically, the oligonucleotide is an aptamer comprises from about 20 bp to about 90 bp.

In a second aspect, the disclosure proposes an L-oligonucleotide aptamer having linked ends. The L-oligonucleotide is not subject to enzymatic degradation and is more stable than naturally occurring oligonucleotides.

In a third aspect, the disclosure proposes a molecule having the structure of 5'-alkyne-L-(rArA) and 3'-azide-L-(rArA) molecule, for appending to the 5' and 3' end of a linear L-Apt.4-1c.

The rArA part of the molecule can be of any design suitable for complementing the activity of the L-RNA.

In a fourth aspect, the disclosure proposes a method of reducing telomerase activity and inhibiting the rG4-protein interaction by using circular L-RNA aptamer.

BRIEF DESCRIPTION OF THE DRAWINGS

The following figures form part of the present specification and are included to further demonstrate certain aspects of the present disclosure. The present disclosure may be better understood by reference to one or more of these figures in combination with the detailed description of specific aspects presented herein.

While the subject matter disclosed herein is susceptible to various modifications and alternative forms, only a few specific aspects have been shown by way of example in the drawings and are described in detail below. The figures and detailed descriptions of these specific aspects are not intended to limit the breadth or scope of the inventive concepts or the appended claims in any manner. Rather, the figures and detailed written descriptions are provided to

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed. (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

The terms "a," "an," "the," etc., are intended to include plural alternatives, e.g., at least one, unless otherwise specified. For instance, the disclosure of "a higher molecular weight component" is meant to encompass one, or mixtures or combinations of more than one, higher molecular weight component, respectively, unless otherwise specified.

Aspects disclosed herein may provide the materials listed as suitable for satisfying a particular feature of the aspect delimited by the term "or." For example, a particular feature of the disclosed subject matter may be disclosed as follows: Feature X can be A, B, or C. It is also contemplated that for each feature the statement can also be phrased as a listing of alternatives such that the statement "Feature X is A, alternatively B, or alternatively C" is also an aspect of the present disclosure whether or not the statement is explicitly recited.

Ribonucleic acid (RNA) aptamers (RNA aptamers and aptamers) are short, single-stranded RNA molecules that fold into stable three-dimensional shapes and are useful for binding to certain structural features of target molecules. RNA aptamers having high affinity and specificity for target molecules, such as proteins, have previously been selected from complex libraries. Most therapeutic RNA aptamers are exogenously administered to cells that express a target molecule (e.g., a target cell) by binding to extracellular domains of certain cell surface proteins. These have been used to inhibit a function of the target molecule or as vehicles to deliver a therapeutic agent to the target cell.

One of the ultimate goals during aptamer selection is a clinical application or an escort molecule. However, naturally occurring nucleic acids are unstable in biological fluids due to enzymatic degradation or a short half-life. Various strategies have been established to increase serum stability and overcome the degradation of oligonucleotides by nuclease.

Aptamers need to be stabilized for in vivo use against nuclease degradation, and their small size makes them susceptible to renal filtration. Aptamers' stabilization can be attained by chemically modifying them using different approaches. Moreover, introducing chemical modifications into nucleic acid libraries increases the interaction capabilities of aptamers and thereby their target spectrum. Modified aptamers may show improved chemical diversity relative to aptamers composed entirely of natural DNA or RNA nucleotides and expand their applications in diagnostics, therapeutics, and nanotechnology.

More recently, the emergence of circular aptamers was reported to overcome the key limitation of instability. Cyclization of nucleic acids by linking 5'- and 3'-termini allows them to escape the primary degradation caused by exonucleases, serving as an easy and reproducible strategy to enhance the resistance of aptamers to nucleases. The cyclization method provides a feasible and efficient way to facilitate applications of the aptamer in diagnosis and therapy through improving their stability to nuclease and binding ability.

L-RNA aptamers (or Spiegelmers) are composed of unnatural L-RNA nucleotides, and not able to hybridize with natural D-RNA through Watson-Crick base-pairing. Given their unnatural nature, L-RNA aptamers are resistant to nucleases degradation, which make them highly biostable in biological fluids and well suited for biomedical applications. Despite the potential applications, L-RNA aptamers have not achieved widespread use. One of the major problems is that there are limited modification and optimization approaches to improve the target recognition properties of L-RNA aptamers, such as conformational stability, binding affinity and specificity. In particular, conformational stability is a significant factor for the successful use of aptamers in complex conditions.

On ongoing need exists for methods and compositions for the chemical modification of aptamer oligonucleotides to enhance their resistance to nuclease degradation. Particularly, new chemistries that modulate L-RNA aptamer structure for enhanced stability, binding affinity and specificity are highly desired.

Disclosed herein are methods and compositions for the cyclization of natural and/or artificial oligonucleotides and aptamers thereof such as L-RNA aptamers. In an aspect, the methods disclose herein result in the efficient cyclization of oligonucleotides such as L-RNA aptamers that result in enhanced binding properties. While described with regard to L-RNA aptamers, other suitable oligonucleotides and aptamers thereof can be cyclized using the processes and compounds described herein.

In an aspect, an aptamer comprises a cyclized L-RNA. Herein L-RNA takes its usual meaning as referring to L-ribonucleic acid aptamer (L-RNA aptamer, trade name Spiegelmer) which is an RNA-like molecule built from L-ribose units. L-RNA is the left-turning and mirror image version of natural RNA, as opposed to the naturally occurring right-turning version called D-RNA. L-RNA is more stable than D-RNA to enzymatic degradation by certain nucleases. Since the two enantiomers are identical in structure other than their chiral differences, their intrinsic physical properties are generally equal to each other. This includes duplex stability, solubility, and selectivity as D-RNA but form a left-helical double-helix. Because of its chiral difference, L-RNA does not bind to its naturally occurring D-RNA counterpart.

In an aspect, an L-RNA of the present disclosure is cyclized to generate a product having enhanced stability. Cyclization of the L-RNA may be carried out using a click-chemistry based reaction. A click-chemistry based reaction that may be utilized in the present disclosure can be based upon the Huisgen 1,3-dipolar cycloaddition between alkynes and azides. Both alkynes and azides are unreactive under physiological conditions and undergo a cycloaddition reaction only at elevated temperatures. Although both alkynes and azide functions can easily be introduced on to the substrates (e.g., L-RNA), the cycloaddition reaction is highly exothermic ($\Delta H_0$ is between −50 and −65 kcal/mol) and has a high activation barrier of 25-26 kcal/mol (for methyl azide and propyne). Hence, the uncatalyzed reaction is generally slow and is not regioselective. These factors limit the use of uncatalyzed Huisgen cycloaddition as an effective conjugation technique. A Cu(I)-catalyzed version of the Huisgen cycloaddition reaction between azides and terminal alkynes is characterized as being about 107 times faster than the uncatalyzed reaction. The Cu(I)-catalyzed reaction is highly regioselective and only the 1,4-adducts are formed. The Cu(I)-catalyzed reactions can be carried out at room temperature.

The present disclosure provides a universal and highly effective click chemistry reaction-based method for L-RNA cyclization. In an aspect, the L-RNA oligos are synthesized to functionalize with a 3'-azide residue and a 5'-hexynyl residue, which can simply introduce a 5' terminal alkyne group. As used herein, a terminal group can also be referred to as a terminal end and refers to the groups on the terminal ends of an oligonucleotide such as L-RNA. In one or more aspects, the 5'-alkyne and 3'-azide terminal groups of an L-RNA is ligated through intramolecular copper(II)-catalyzed azide-alkyne cycloaddition with high efficiency. For example, the efficiency of the reaction with Cu(II) for formation of a cyclized L-RNA is from about 70% to about 99%, alternatively from about 80% to about 990% or alternatively from about 90% to about 99%. In an aspect, about 95% of the linear L-RNA can be converted into cyclized form In an aspect, the methods disclosed herein may be utilized to cyclize any suitable (e.g., short) L-RNA with whose 5' end is close to its 3' end. For example, the L-RNA may comprise from about 20 basepairs (bp) to about 90 bps, alternatively from about 25 bp to about 80 bp or alternatively from about 25 bp to about 75 bp. In an aspect, the LRNA can be functionalized with a 3'-azide residue and a 5' terminal alkyne group (e.g., 5'-hexynl residue).

In an aspect, L-RNA may be present in a reaction of the type disclosed herein in an amount of 2 pmol to 100 nmol.

A cyclization reaction of the type disclosed herein may be carried out in the presence of a catalyst. Catalysts suitable for use include without limitation copper, alternatively copper (I). In an aspect, the molecule comprises a copper (II) complex with the ligand tris(benzyltriazolylmethyl)amine, designated Cu(II)-TBTA, having general Structure 1. Cu(II)-TBTA is reduced to Cu(I) by ascorbic acid and functions as a catalyst.

Structure I

Catalyst (e.g., Cu(II)-TBTA) may be present in a reaction of the type disclosed herein in an amount of 100 pmol to 5 pmol. In an aspect, a method of the present disclosure comprises cyclization of the L-RNA. Cyclization of the L-RNA may initiate with denaturation of the L-RNA. Denaturation of the L-RNA may be carried out using any suitable methodology. For example, the L-RNA may be denatured thermally, such as by being subjected to a high temperature (e.g., greater than about 90° C.). Denatured L-RNA, designated d-L-RNA, may be cooled such as being placed on ice. The d-L-RNA can then be contacted in a suitable vessel with the Cu(II) agent (e.g., Cu(II)-TBTA) and a reducing agent (e.g., ascorbic acid). Advantageously, the cyclization reaction can be carried out at mild temperatures such as less than about 50° C., alternatively less than about 40° C. or alternatively about 37° C.

In one or more aspects, the methods disclosed herein may be used to functionalize L-RNA oligos like L-RNA aptamer for further application. Further, the present disclosure demonstrates that the head-to-tail cyclization can be an effective way to strengthen the function of L-RNA aptamer, which enables its applications in buffer or complex biological conditions. The presently disclosed subject matter may be applicable for aptamer studies, but also potentially to other functional L-RNAs, such as for L-RNA hairpins, which are easy to be unfolded when conditions change. In summary, presently disclosed cyclization strategy will be useful in preparing stable L-RNA constructs for structural studies and function optimization.

EXAMPLES

The subject matter having been generally described, the following examples are given as particular aspects of the disclosure and are included to demonstrate the practice and advantages thereof, as well as preferred aspects and features of the inventions. It should be appreciated by those of skill in the art that the techniques disclosed in the examples which follow represent techniques discovered by the inventors to function well in the practice of the inventions, and thus can be considered to constitute preferred modes for its practice. However, those of skill in the art should, in light of the present disclosure, appreciate that many changes can be made in the specific aspects which are disclosed and still obtain a like or similar result without departing from the scope of the inventions of the instant disclosure. It is understood that the examples are given by way of illustration and are not intended to limit the specification of the claims to follow in any manner.

Example 1

The ability of the methods disclosed herein to cyclize an L-RNA was investigated. Specifically, G-quadruplexes (G4s) are nucleic acid structure motifs that are of significance in chemistry and biology. The function of G4s is often governed by their interaction with G4-binding proteins. An L-RNA aptamer that can generally bind to D-RNA G-quadruplex (rG4) structure, and interfere with rG4-protein interaction is hTERC rG4 as the target for in vitro selection. L-Apt.4-1c is a 25-nucleotide aptamer that adopts a stem-loop structure with the loop folding into an rG4 motif with two G-quartet and demonstrates preferential binding toward rG4s over non-G4s and DNA G-quadruplexes (dG4s), and suppresses hTERC rG4-nucleolin interactions. Cyclization of L-Apt.4-1c was investigated and the reaction schematized in FIG. 1.

Cyclization of L-Apt.4-1c by Click Chemistry Reaction

Figure 1:
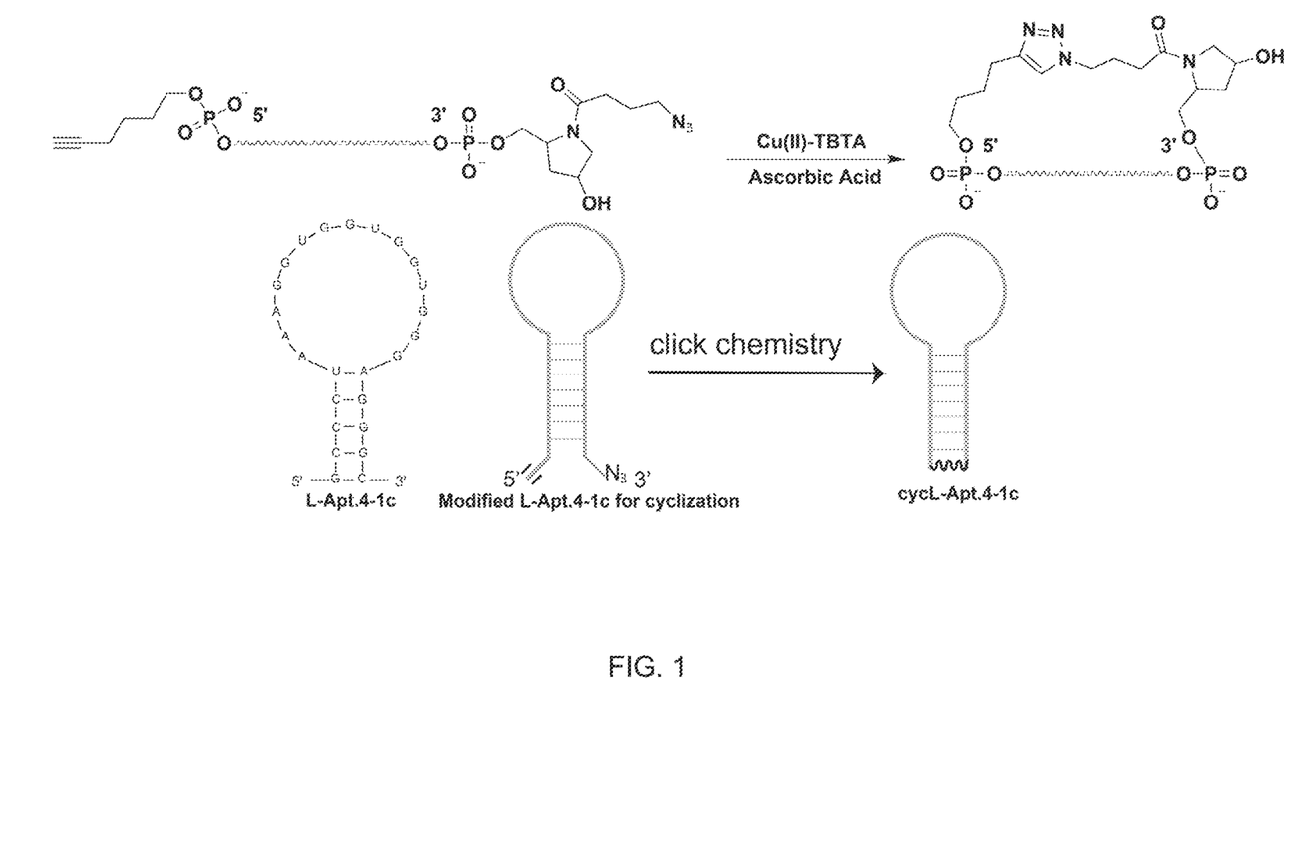
FIG. 1 is a schematic representation of the preparation and structure of cyclized L-RNA aptamer (cycL-Apt.4-1c), in which the Apt.4-1c has the nucleotide sequence of "GCCCUAAAGGUGGUGGUGGGAGGGC" (from 5' end to 3' end; SEQ ID NO: 1).

The 5'-alkyne and 3'-azide labelled L-Apt.4-1c oligonucleotide was dissolved by nuclease-free ultrapure distilled water to get a stock solution of 100 μM. L-Apt.4-1c (500 nM) was denatured at 95° C. for 3 min in Tris-HCl buffer (25 mM Tris, 50 mM K$^+$, and 5 mM Mg$^{2+}$, pH 7.5) and then quickly cooled down on ice before cyclization. The cyclization conditions were as follows; 25 µM Cu(II)-TBTA and 250 µM freshly prepared ascorbic acid were added to L-Apt.4-1c. The click chemistry reaction was carried out at 37° C. for 2 h. The reaction solution was then desalted using ZYMO-SPIN IC Columns and analyzed on 12% denaturing polyacrylamide gel (PAGE) with SYBR Gold staining. This reaction is schematized in FIG. 1. Referring to FIG. 1, alkyne and azide residues were modified at 5' and 3' of L-RNA oligo, respectively. In the presence of ascorbic acid (AA) and Cu(II)-TBTA, Cu$^{2+}$ is reduced to Cu$^+$ by AA. Cu$^+$ catalyzes the occurrence of click chemistry reaction between alkyne and azide group, producing cyclized L-RNA. The cyclization of L-RNA aptamer described in these examples, i.e., L-Apt.4-1c, is exemplary and not meant to limit the type of L-RNA that may be cyclized utilizing the methodologies disclosed herein.

Figure 2A:
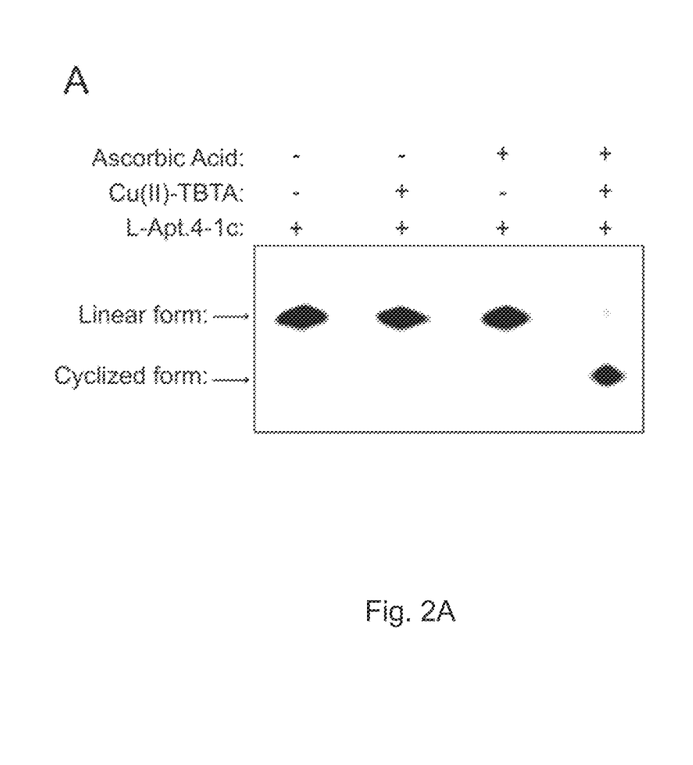
FIG. 2A is a picture of a denaturing gel of the sample from Example 1.

The results of PAGE are presented in FIG. 2A. Referring to FIG. 2A, denaturing PAGE gel shows cyclization results of L-Apt.4-1c.

Fluorescence Detection of cycL-Apt.4-1c with ThT.

Figure 2B:
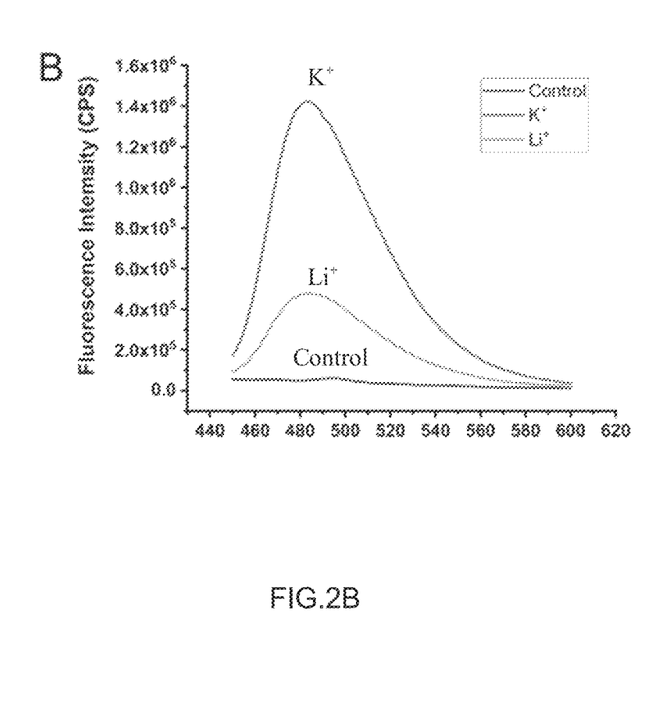
FIG. 2B are fluorescence emission spectra for the samples from Example 1.

Fluorescence detection was performed on a HORIBA FLUOROMAX-4 fluorescence spectrophotometer (Japan) using 1-cm path length quartz cuvette. CycL-Apt.4-1c (300 nM) was heated at 95° C. for 3 min and cooled down on ice for 10 min before use. A fluorescent dye, thioflavin T (ThT) (2 µM), was mixed with cycL-Apt.4-1c in Tris-HCl buffer (25 mM Tris, 150 mM K$^+$/Li$^+$, and 1 mM Mg$^{2+}$, pH 7.5). The samples were incubated at room temperature for 30 min followed by fluorescence measurement. Spectra of ThT were excited at 425 nm and scanned from 450 nm to 600 nm. Excitation and emission slits were set at 5 nm and the results are shown in FIG. 2B. Fluorescence emission spectra of ThT with cycL-Apt.4-1c (300 nM) under 150 mM KCl and LiCl condition. The strong fluorescence under K$^+$ condition suggests the formation of rG4 structure in cycL-Apt.4-1c. ThT only in Tris-HCl buffer with 150 mM K$^+$ was used as the control.

Electrophoretic Mobility Shift Assay (EMSA).

Figure 2C:
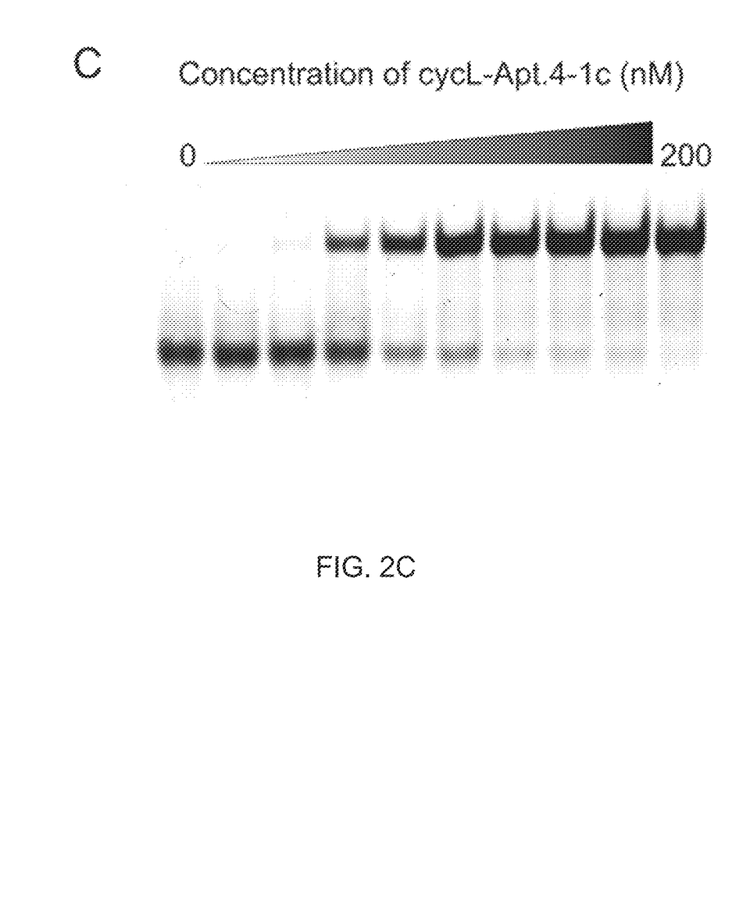
FIG. 2C is a picture of an electrophoretic mobility shift assay gel.
Figure 2D:
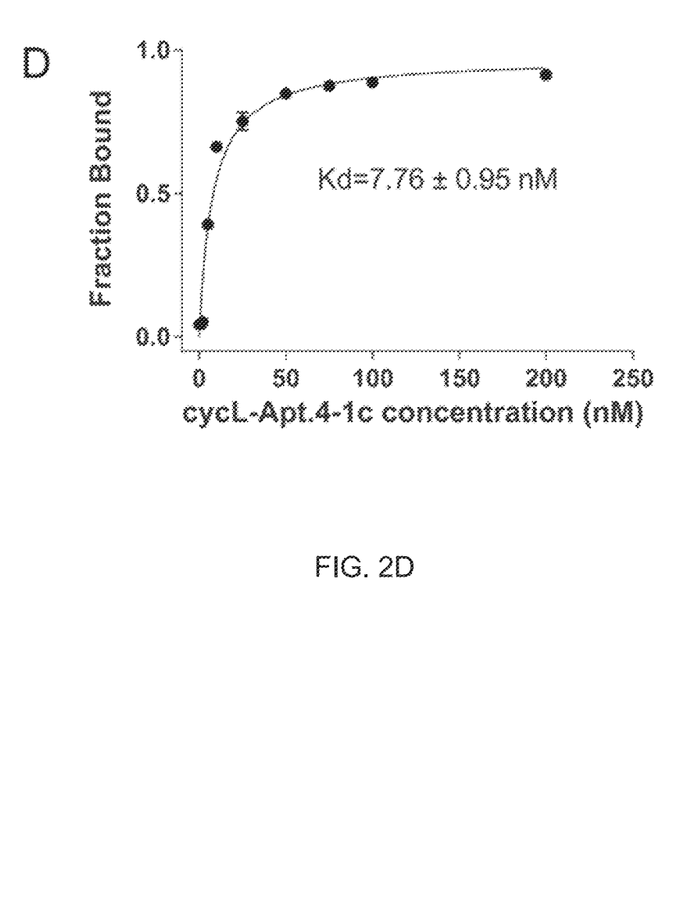
FIG. 2D is a graph of the binding curve for the samples from Example 1.

CycL-Apt.4-1c was heated at 75° C. for 3 min and cooled down at room temperature for 10 min before use. FAM (fluorescein amidite)-labelled hTERC rG4 (30 nM) was mixed with different concentrations of cycL-Apt.4-1c (0-200 nM) in Tris-HCl buffer (25 mM Tris, 150 mM K$^+$, and 1 mM Mg$^{2+}$, pH 7.5), and incubated at 37° C. for 30 min. Sucrose (8%) was added to samples before loading onto a 12% native PAGE (19:1, acrylamide:bis-acrylamide). The gel was prepared with Tris-HCl buffer (25 mM Tris, 50 mM K$^+$, and 1 mM Mg$^{2+}$, pH 7.5), which was also used as running buffer. The electrophoresis was carried out at 4° C. for 50 min with a consistent current at 70 mA. The gel was scanned by FUJIFILM FLA-9000 Gel Imager at 650 V and quantified by ImageJ and the results presented in FIG. 2C. The binding curve was fitted using GRAPHPAD PRISM with the one site-specific binding model and the results are presented in FIG. 2D. EMSA shows the binding between cycL-Apt.4-1c (0-200 nM) and target FAM-hTERC rG4. With increasing concentration of cycL-Apt.4-1c, the bound band (upper band) became darker, whereas the unbound band (lower band) became weaker. This suggested the strong interaction between cycL-Apt.4-1c and FAM-hTERC rG4. The dissociation constants (K$_d$) were calculated to be 7.76±0.95 nM.

Specificity Test of cycL-Apt.4-1c to hTERC rG4.

Figure 3:
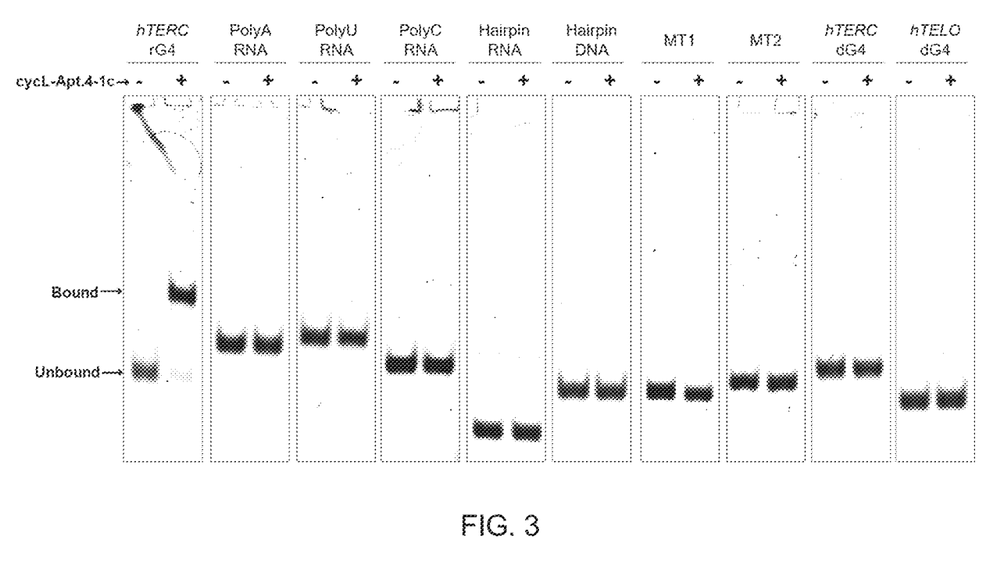
FIG. 3 is a native gel demonstrating the specificity of the samples from Example 1.

FAM-labelled hTERC rG4 (30 nM) and other DNA/RNA oligos (30 nM) were mixed with 100 nM of pre-annealed cycL-Apt.4-1c in Tris-HCl buffer (25 mM Tris, 150 mM K$^+$, and 1 mM Mg$^{2+}$, pH 7.5). Then the samples were incubated at 37° C. for 30 min. After that, sucrose (8%) was added and samples were loaded to a 12% native PAGE. The performing and analysis procedure of PAGE were the same as EMSA section and the results are demonstrated in FIG. 3. Referring to FIG. 3, Native PAGE gel (12%) shows that only hTERC rG4 interacted with cycL-Apt.4-1c and caused gel shift, whereas the other DNA/RNA constructs have no obvious binding to cycL-Apt.4-1c. MT1: hTERC rG4 mutant type 1. MT2: hTERC rG4 mutant type 2.

Competitive Inhibition of HTERC rG4-DHX36 Binding by cycL-Apt.4-1c

Figure 4A:
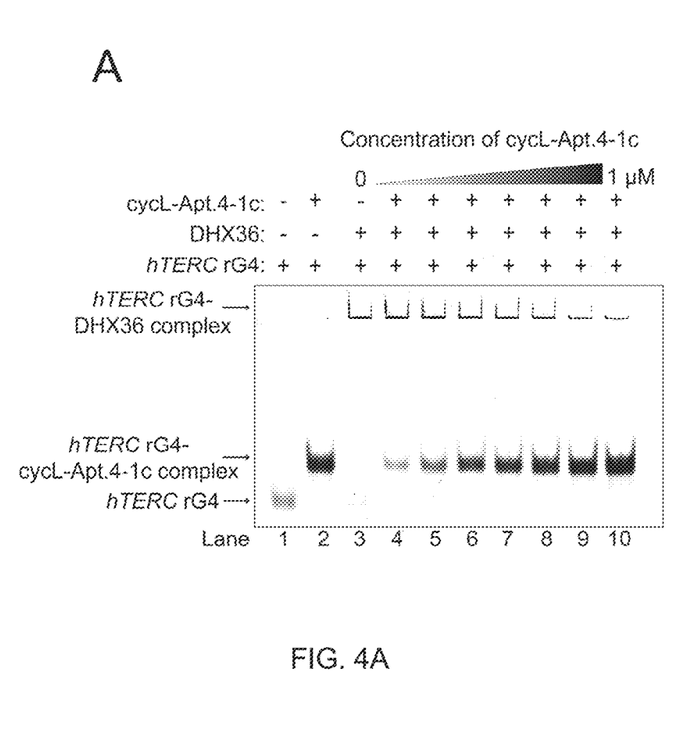
FIG. 4A demonstrates the results of competitive inhibition assays.
Figure 4B:
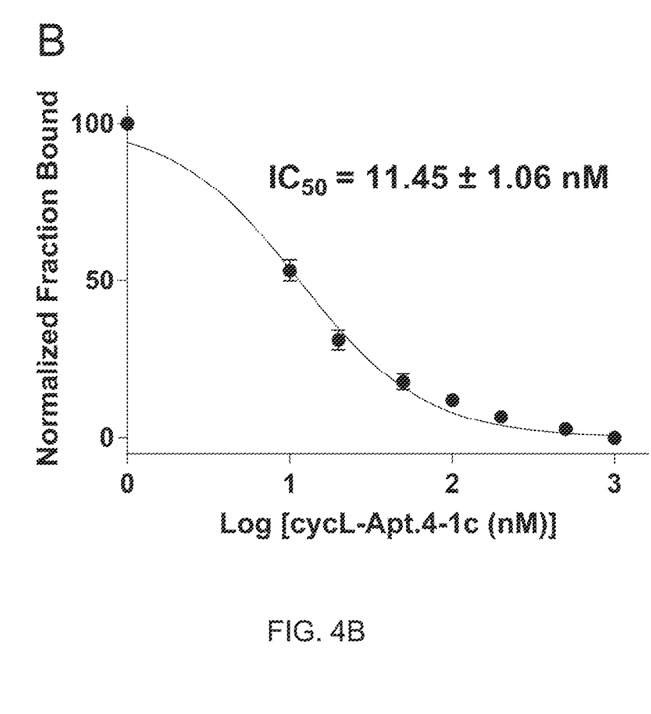
FIG. 4B is the inhibition curve of cycL-Apt.4-1c on hTERC D-rG4-DHX36 complex generated from data in FIG. 4A.

FAM-labelled hTERC rG4 (30 nM) was mixed with different concentrations of cycL-Apt.4-1c (0-1 µM) and DHX36 (100 nM) in Tris-HCl buffer (25 mM Tris, 150 mM K$^+$, and 1 mM Mg$^{2+}$, pH 7.5). DHX36, also known as RNA helicase associated with AU-rich elements (RHAU) is a 1008 amino acid-long modular protein that has been reported to associate with hTERC D-rG4 to interfere telomerase activity The mixtures were incubated at 37° C. for 30 min and loaded to a 8% native PAGE (37.5:1, acrylamide: bis-acrylamide). The gel was performed at 70 mA for 30 min and the results are presented in FIG. 4A. EMSA shows that the binding of DHX36 and FAM-hTERC rG4 is inhibited by cycL-Apt.4-1c. With increasing concentration of cycL-Apt.4-1c (lanes 4-10), the hTERC rG4-DHX36 complex (upper bands) get weaker, while the rG4-cycL-Apt.4-1c complex becomes stronger (lower bands). This suggests the interaction of hTERC rG4 and DHX36 can be inhibited by cycL-Apt.4-1c. Inhibition curve of cycL-Apt.4-1c on hTERC rG4-DHX36 complex formation was fitted by GRAPHPAD PRISM using the dose-response inhibition model was prepared and the results are presented in FIG. 4B. The inhibition curve of cycL-Apt.4-1c on hTERC rG4-DHX36 complex formation was used to determine and IC$_{50}$ of 11.45 nM.

Telomerase Repeated Amplification Protocol (TRAP) Assay

Figures 4C, 4D:
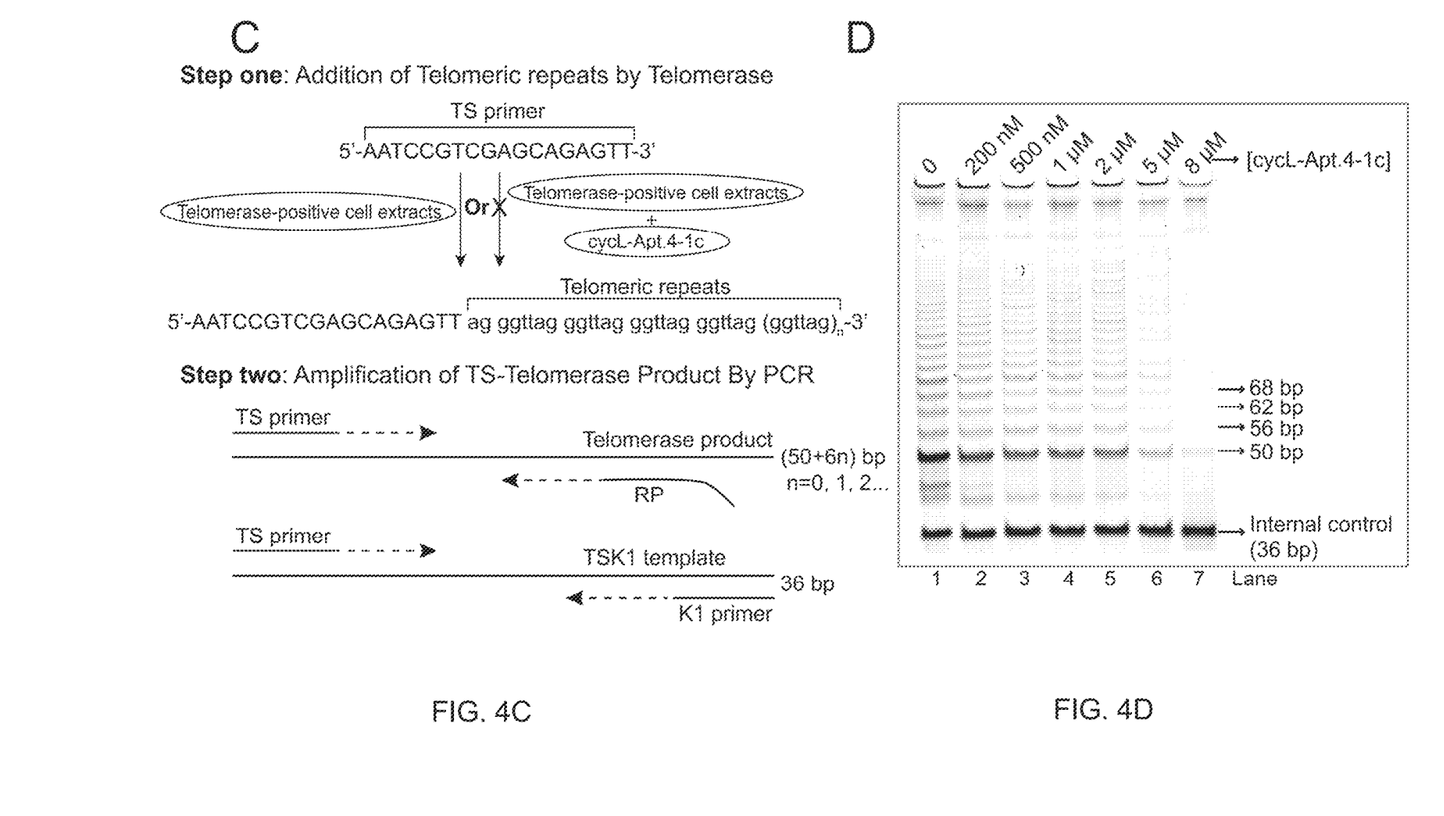
FIG. 4C is the workflow of the TRAP assay, in which the TS primer has the nucleotide sequence of "AATCCGTCGAGCAGAGTT" (from 5' end to 3' end; SEQ ID NO: 2), and the telomeric repeat has the nucleotide sequence of "AATCCGTCGAGCAGAGTTAGGGTTAGGGTTAGGGTTAGGGTTAGGGTTAG" (from 5' end to 3' end; SEQ ID NO: 3) with a 3' tail of (ggttag)$_n$.
FIG. 4D is a gel depicting the results of the telomerase inhibition assay.

A commercial TRAPEZE® gel-based telomerase detection kit (Merck Millipore) was used in this experiment. In accordance with the manufacturer's instructions, a three-step TRAP procedure was performed: (i) addition of telomeric repeats to the telomerase substrate by telomerase, (ii) amplification of telomerase product by PCR, (iii) detection of telomerase products by electrophoresis (FIG. 4C). Under best conditions, cell extracts (500 cell/µl) were mixed with different concentrations of pre-annealed cycL-Apt.4-1c (0-8 µM) in Tris-HCl buffer (25 mM Tris, 150 mM K$^+$, and 1 mM Mg$^{2+}$, pH 7.5) and incubated at 37° C. for 1 h. Then 1 µl (500 cell) of the reaction mixture was added to pre-prepared master mix containing TRAP buffer, dNTP, primers and Taq polymerase. After that, the samples were allowed to incubate at 30° C. for 30 min for extension followed by 30-cycle PCR reaction. Reaction products were run on an 8% native PAGE and stained with SYBR gold and the results are presented in FIG. 4D which is a native gel (8%) that was used to analyze the results of TRAP assay. Referring to FIG. 4D, Lane 1 was 500 cells without cycL-Apt.4-1c while lanes 2-7 were samples having 500 cells with the indicated concentrations of cycL-Apt.4-1c. It was observed that with increasing concentrations of cycL-Apt.4-1c, the intensity of the whole lane got weaker and weaker, which suggested that cycL-Apt.4-1c can bind to hTERC rG4 an inhibit telomerase activity.

Dual Luciferase Reporter Gene Assay

Figure 5A:
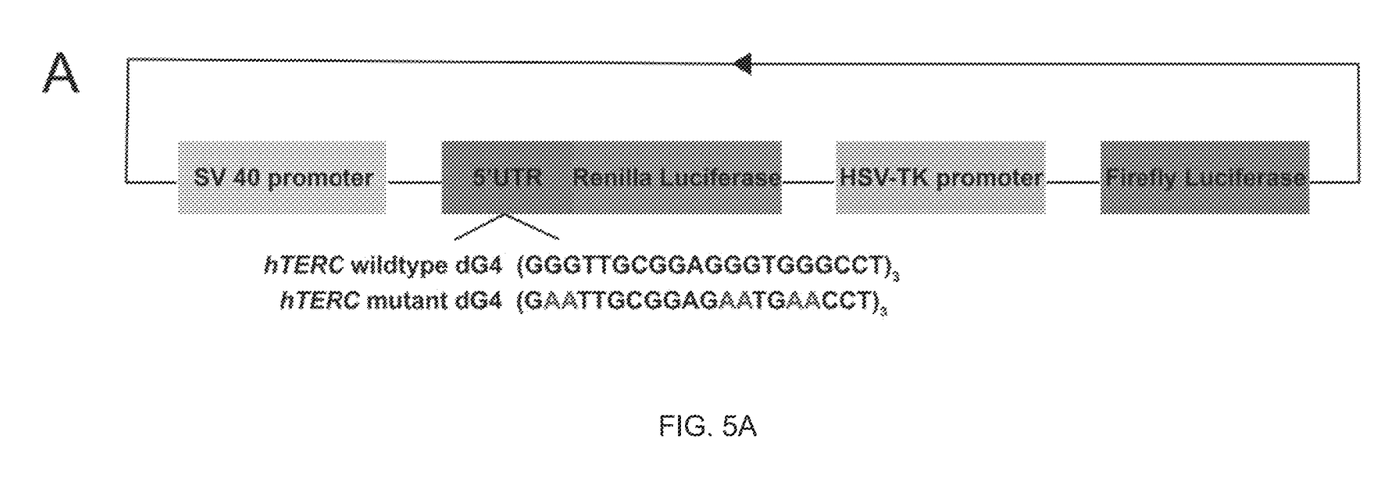
FIG. 5A is the schematic illustration of the design of luciferase reporter plasmids, in which hTERC wildtype dG4 and hTERC mutant dG4 respectively have the nucleotide sequences of "GGGTTGCGGAGGGTGGGCCTAAAGGGTTGCGGAGGGTGGGCCTAAAGGGTTGCGGAGGGTGGGCCT" (from 5' end to 3' end; SEQ ID NO: 4) and "GAATTGCGGAGAATGAACCTAAAGAATTGCGGAGAATGAACCTAAAGAATTGCGG AGAATGAACCT" (from 5' end to 3' end; SEQ ID NO: 5).
Figure 5B:
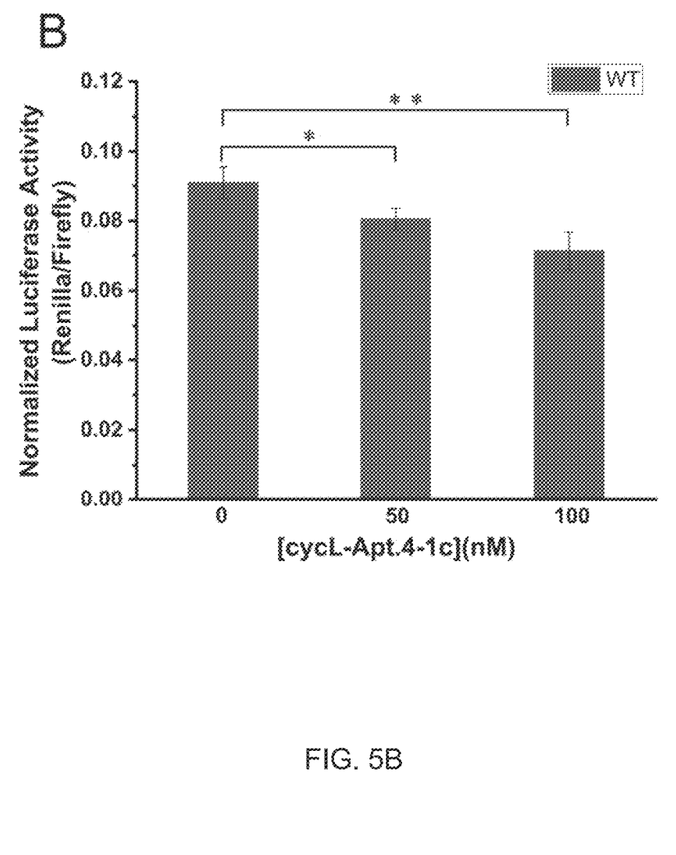
FIG. 5B Normalized luciferase activity of cells transfected with hTERC dG4 wildtype plasmid (WT) and cycL-Apt.4-1c.
Figure 5C:
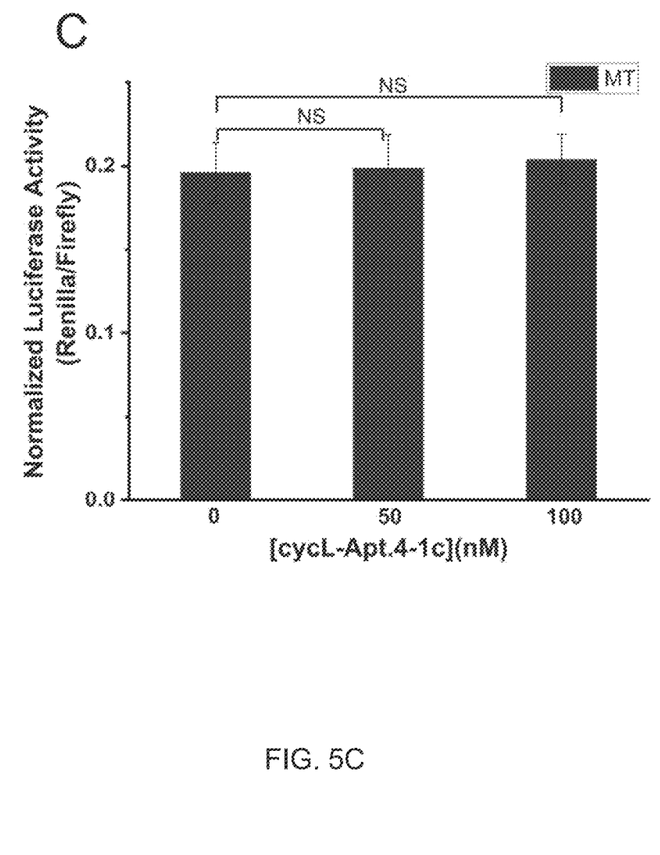
FIG. 5C Normalized luciferase activity of cells transfected with hTERC dG4 mutant plasmid (MT) and cycL-Apt.4-1c.

Firefly/*Renilla* dual luciferase reporter vector, psi-CHECK-2 was used in this assay. Wildtype and mutant hTERC D-G4 DNA sequences were inserted into the 5' terminal of *Renilla* luciferase gene at the NheI restriction enzyme site by Genewiz (FIG. 5A). Wildtype and mutant reporter plasmids were mixed with 0 nM, 50 nM and 100 nM cycL-Apt.4-1c or cycD-Apt.4-1c and transfected into HEK293T cells (cell line authenticated and tested without *mycoplasma* contamination) in 96-well black-wall optical plates using Lipofectamine® 2000 with 10 ng plasmids each well. The DMEM medium (Gibco) supplemented with 10% heat-inactivated fetal bovine serum (Gibco) was changed to fresh medium after 24 h of transfection, and cells were incubated for another 24 h. Then luciferase reporter gene assay was conducted using Dual-Luciferase Reporter Assay kit according to the manufacturer's manual. Luciferase activities were recorded by Molecular Devices SpectraMax ID5 Microplate Reader. The intensity of firefly luciferase is used as an internal control. The luciferase activity ratio of *Renilla* to firefly was calculated for data analysis. All the measurements were performed with four replicates and the standard deviation was plotted as the error bar. The significance level of samples was evaluated using P-value obtained from two-tailed unpaired Student's t tests.

Total RNA Extraction and qRT-PCR Test

The transfection and cell incubation processes are the same as mentioned above for reporter gene assay. After pelleting cells, total RNA was extracted and purified using RNase Plus Mini Kit following the manufacturer's manuals. The concentrations of total RNA samples were detected by NanoDrop spectrophotometer (Thermo Fisher Scientific, USA). Then 100 ng of total RNA was reverse transcribed to cDNA using SuperScript III reverse transcriptase and random primers. After that, qRT-PCR tests for Firefly and *Renilla* mRNA were conducted, respectively with SsoAdvanced Universal SYBR Green Supermix and corresponding primers using a Bio-Rad CFX96 Touch™ Real-Time PCR Detection System (USA). All the samples were performed with three replicates and the standard deviation was plotted as the error bar. The significance level of samples was evaluated using P-value obtained from two-tailed unpaired Student's t tests.

Additional Disclosure

The following is provided as additional disclosure for combinations of features and aspects of the presently disclosed subject matter.

A first aspect which is a method of cyclizing an aptamer comprising denaturing an aptamer to form a denatured aptamer wherein the aptamer has a 3' azide residue and a 5' terminal alkyne group; and contacting the denatured aptamer with a copper-tertiary amine complex in the presence of a reducing agent under conditions suitable to form a cyclized aptamer.

A second aspect which is a method of the first aspect wherein the aptamer comprises L-RNA.

A third aspect which is the method of any of the first through second aspects wherein the aptamer comprises from about 20 bp to about 90 bp.

A fourth aspect which is the method of any of the first through third aspects wherein the copper tertiary amine complex comprises a copper (II) complex with the ligand tris(benzyltriazolylmethyl)amine.

A fifth aspect which is the method of any of the first through fourth aspects wherein the aptamer is present in an amount of 2 pmol to 100 nmol.

A sixth aspect which is the method of any of the first through fifth aspects wherein the copper-tertiary amine complex is present in an amount of 100 pmol to 5 µmol.

A seventh aspect which is the method of any of the first through sixth aspects wherein the reducing reagent comprises ascorbic acid.

An eighth aspect which is the method of any of the first through seventh aspects of claim 1 having an efficiency of about 95%.

A ninth aspect which is a method of cyclizing an aptamer comprising contacting L-RNA with a copper(II) molecule and ascorbic acid.

A tenth aspect which is the method the ninth aspect wherein the aptamer comprises from about 20 bp to about 90 bp.

An eleventh aspect which is the method of any of the ninth through tenth aspects, wherein the L-RNA is present in an amount of 2 pmol to 100 nmol.

A twelfth aspect which is the method of any of the ninth through eleventh aspects wherein the copper reagent comprises a copper (II) complex with the ligand tris(benzyltriazolylmethyl)amine.

A thirteenth aspect which is the method of any of the tenth through twelfth aspects wherein the L-RNA is present in an amount of 2 pmol to 100 nmol.

A fourteenth aspect which is the method of any of the ninth through thirteenth aspects wherein the copper molecule comprises a copper (II) complex with the ligand tris(benzyltriazolylmethyl)amine.

A fifteenth aspect which is the method of any of the ninth through fourteenth aspects wherein the copper (II) complex with the ligand tris(benzyltriazolylmethyl)amine is present in in an amount of 100 pmol to 5 µmol.

A sixteenth aspect which is the method of any of the ninth through fifteenth aspects wherein the ascorbic acid is present in an amount of 1 nmol to 50 µmol.

A seventeenth aspect which is the method of any of the ninth through sixteenth aspects wherein the L-RNA has a 3' azide residue and a 5' terminal alkyne.

An eighteenth aspect which is a method of cyclizing an aptamer comprising synthesizing an L-RNA aptamer with a 3' azide residue and a 5' terminal alkyne group; and ligating the -RNA aptamer with a 3' azide residue and a 5' terminal alkyne group using intramolecular click chemistry reaction under the catalysis of Cu(II)-tris(benzyltriazolylmethyl) amine and ascorbic acid to form a cyclized aptamer.

A nineteenth aspect which is the method of the eighteenth aspect wherein the L-RNA is present in an amount of 2 pmol to 100 nmol.

A twentieth aspect which is the method of the eighteenth through nineteenth aspects wherein the ascorbic acid is present in an amount of 1 nmol to 50 µmol.

In a twenty first aspect, a method of linking two terminal ends of oligonucleotide wherein one of the terminal oligonucleotide ends has a 5' terminal alkyne; and the other one of the terminal oligonucleotide ends has a 3' azide residue; comprising the step of: linking the 5' terminal alkyne to the 3' azide residue.

A twenty second aspect can include the method of the twenty first aspect, wherein the step of linking the 5' terminal alkyne to the 3' azide residue to place in the presence of a catalyst for azide-alkyne cycloaddition.

A twenty third aspect can include the method of the twenty second aspect, wherein the catalyst is Cu(I).

A twenty fourth aspect can include the method of the twenty third aspect, wherein the step of providing a catalyst for azide-alkyne cycloaddition comprises providing Cu in a higher oxidation state; and a reducing agent to reduce the Cu in a higher oxidation state to Cu(I)

A twenty fifth aspect can include the method of the twenty third or twenty fourth aspects, wherein the Cu is provided in the form of copper (II) complex with the ligand tris(benzyltriazolylmethyl)amine.

A twenty sixth aspect can include the method of the twenty fourth aspect, wherein the reducing agent is ascorbic acid or its salt.

A twenty seventh aspect can include the method of the twenty fourth aspect, wherein the Cu in a higher oxidation state is Cu(II)-TBTA.

A twenty eighth aspect can include the method of any one of the twenty first to twenty seventh aspects, wherein the two terminal ends of oligonucleotide are from a single strand of RNA.

A twenty ninth aspect can include the method of the twenty eighth aspect, wherein the single strand of RNA is L-Apt.4-1c.

A thirtieth aspect can include the method of any one of the twenty first to twenty seventh aspects, wherein the two terminal ends of oligonucleotide are from two unconnected strands of RNA.

A thirty first aspect can include the method of any one of the twenty first to thirtieth aspects, wherein the oligonucleotide is an aptamer comprises from about 20 bp to about 90 bp.

In a thirty second aspect, an L-oligonucleotide aptamer has linked ends.

A thirty third aspect can include the L-oligonucleotide aptamer of the thirty second aspect, wherein the linkage of the linked ends is between 5'-alkyne on one end and 3'-azide on another other end.

In a thirty fourth aspect, a molecule has the structure of 5'-alkyne-L-(rArA) and 3'-azide-L-(rArA) molecule, for appending to the 5' and 3' end of a linear L-Apt.4-1c.

In a thirty fifth aspect, a method of reducing telomerase activity comprises the step of providing circular L-RNA aptamer to inhibit the rG4-protein interaction.

While aspects of the disclosure have been shown and described, modifications thereof can be made without departing from the spirit and teachings of the disclosed subject matter. The aspects and examples described herein are exemplary only, and are not intended to be limiting. Many variations and modifications of the subject matter disclosed herein are possible and are within the scope of the disclosed subject matter.

At least one aspect is disclosed and variations, combinations, and/or modifications of the aspect(s) and/or features of the aspect(s) made by a person having ordinary skill in the art are within the scope of the disclosure. Alternative aspects that result from combining, integrating, and/or omitting features of the aspect(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the detailed description of the presently disclosed subject matter.

What is claimed is:

1. A method of linking two terminal ends of oligonucleotide, wherein one of the terminal oligonucleotide ends has a 5' terminal alkyne; and the other one of the terminal oligonucleotide ends has a 3' azide residue; comprising the step of:
    linking the 5' terminal alkyne to the 3' azide residue,
    wherein the oligonucleotide is L-Apt.4-1c comprising the nucleotide sequence of SEQ ID NO: 1.

2. A method of joining two terminal ends of an oligonucleotide as claimed in claim 1, wherein the step of linking the 5' terminal alkyne to the 3' azide residue is carried out in the presence of a catalyst for azide-alkyne cycloaddition.

3. A method of joining two terminal ends of an oligonucleotide as claimed in claim 2, wherein the catalyst is Cu(I).

4. A method of joining two terminal ends of an oligonucleotide as claimed in claim 3, wherein the step of providing a catalyst for azide-alkyne cycloaddition comprises:
    providing Cu in a higher oxidation state; and
    a reducing agent to reduce the Cu in a higher oxidation state to Cu(I).

5. A method of joining two terminal ends of an oligonucleotide as claimed in claim 4, wherein the Cu is provided in the form of copper (II) complex with the ligand tris(benzyltriazolylmethyl)amine.

6. A method of joining two terminal ends of an oligonucleotide as claimed in claim 4, wherein the reducing agent is ascorbic acid or its salt.

7. A method of joining two terminal ends of an oligonucleotide as claimed in claim 4, wherein the Cu in a higher oxidation state is Cu(II)-TBTA.

\* \* \* \* \*

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial sequence
<220> FEATURE:
<223> OTHER INFORMATION: synthetic construct

<400> SEQUENCE: 1
gccctaaagg tggtggtggg agggc                                           25

<210> SEQ ID NO 2
<211> LENGTH: 18
<212> TYPE: DNA
<213> ORGANISM: Artificial sequence
<220> FEATURE:
<223> OTHER INFORMATION: synthetic construct

<400> SEQUENCE: 2
```

```
aatccgtcga gcagagtt                                                    18

<210> SEQ ID NO 3
<211> LENGTH: 50
<212> TYPE: DNA
<213> ORGANISM: Artificial sequence
<220> FEATURE:
<223> OTHER INFORMATION: synthetic construct

<400> SEQUENCE: 3
aatccgtcga gcagagttag ggttagggtt agggttaggg ttagggttag                 50

<210> SEQ ID NO 4
<211> LENGTH: 66
<212> TYPE: DNA
<213> ORGANISM: Artificial sequence
<220> FEATURE:
<223> OTHER INFORMATION: synthetic construct

<400> SEQUENCE: 4
gggttgcgga gggtgggcct aaagggttgc ggagggtggg cctaaagggt tgcggagggt      60
gggcct                                                                 66

<210> SEQ ID NO 5
<211> LENGTH: 66
<212> TYPE: DNA
<213> ORGANISM: Artificial sequence
<220> FEATURE:
<223> OTHER INFORMATION: synthetic construct

<400> SEQUENCE: 5
gaattgcgga gaatgaacct aaagaattgc ggagaatgaa cctaaagaat tgcggagaat      60
gaacct                                                                 66
```